United States Patent
Kadhiresan et al.

[11] Patent Number: 5,931,858
[45] Date of Patent: Aug. 3, 1999

[54] IMPLANTABLE DEVICE FOR MONITORING AEROBIC CAPACITY OF PATIENTS

[75] Inventors: Veerichetty A. Kadhiresan, Lino Lakes; Arthur L. Olive, Stacy; Bruce R. Jones, Hopkins, all of Minn.

[73] Assignee: Cardiac Pacemakers, Inc., St. Paul, Minn.

[21] Appl. No.: 09/005,501

[22] Filed: Jan. 12, 1998

[51] Int. Cl.⁶ .................................................. A61N 1/00
[52] U.S. Cl. ................................................................ 607/20
[58] Field of Search .................................. 600/534, 595; 607/19, 20

[56] References Cited

U.S. PATENT DOCUMENTS

| | | | |
|---|---|---|---|
| 4,428,378 | 1/1984 | Anderson et al. | 607/19 |
| 4,722,342 | 2/1988 | Amundson | 607/20 |
| 5,044,366 | 9/1991 | Alt | 607/19 |
| 5,603,331 | 2/1997 | Heemels et al. | 128/696 |
| 5,694,939 | 12/1997 | Cowins | 607/20 |

*Primary Examiner*—Max Hindenburg
*Attorney, Agent, or Firm*—Nikolai, Mersereau & Dietz, P.A.

[57] ABSTRACT

An implantable electronic circuit for monitoring a patient's aerobic capacity includes an accelerometer for detecting the onset and termination of a period of exercise and a means for measuring the patient's minute volume. By computing the time interval from the cessation of exercise to the point where the patient's minute volume reaches a predetermined value at or near an at-rest value thereof, a measure of aerobic capacity relating to a patient's physical fitness can be determined.

13 Claims, 5 Drawing Sheets

IMPLANTABLE DEVICE FOR MONITORING AEROBIC CAPACITY OF PATIENTS

BACKGROUND OF THE INVENTION

I. Field of the Invention

This invention relates generally to implantable electronic monitoring apparatus, and more particularly an implantable electronic device for monitoring aerobic capacity of patients.

II. Discussion of the Prior Art

A typical prior art pacemaker of the rate adaptive type has commonly incorporated one or more sensors for detecting a physiologic function and for producing an electrical control signal proportional thereto. The electrical control signal is then applied to the timing circuitry of the pacemaker for adjusting the rate at which cardiac stimulating pulses are produced from a programmed lower rate limit to a similarly programmed upper rate limit. Physiologic sensors have included accelerometers for detecting body motion and, in this regard, reference is made to the Meyerson et al. U.S. Pat. No. 5,179,947. Other physiologic parameters that change with hemodynamic need include blood temperature (Cook et al. U.S. Pat. No. 4,436,092), oxygen saturation (Wertzfeld et al. U.S. Pat. No. 4,202,339), the heart's preejection interval (Citak et al. U.S. Pat. No. 4,773,401) as well as respiratory factors including tidal volume (Alt U.S. Pat. No. 4,919,136), respiration rate (Krasner U.S. Pat. No. 3,593,718) and the product thereof, minute ventilation (Plicchi et al. U.S. Pat. No. 4,596,251). These respiratory factors can be derived from the accelerometer output signal using signal processing techniques to isolate components of body motion due to breathing. Alternatively, electrodes may be provided for measuring variations in electrical impedance between electrodes placed in the thoracic cavity.

Implantable cardiac pacemakers are now also being used in treating patients suffering from congestive heart failure (CHF). It has been found that the efficiency of the heart as a pump can be improved by pacing the ventricles with an optimum AV delay between the occurrence of an intrinsic atrial depolarization and the application of a ventricular stimulating pulse.

From the foregoing, it is clear that the technology exists for incorporating within an implantable, fluid impermeable, body compatible housing electronic circuitry including a microprocessor-based controller that is adapted to receive the output from a variety of physiologic sensors including accelerometers and means for sensing respiratory parameters for controlling a pulse generator whose output is used to stimulate the atrium, the ventricles or both.

In addition to the pacing function, implantable cardiac rhythm management devices are increasingly taking advantage of the increase in memory capacity of microprocessors to monitor and store a variety of parameters for later read-out over a telemetry link to an external monitor/programmer module. For example, heart rate variability over a period of many days may be calculated and stored for later read-out. See Heemels et al. U.S. Pat. No. 5,603,331. Heart rate variability has been found to be a significant indicator of the progress of CHF.

Another measure of the efficacy of treatment by drugs, pacing or a combination thereof is the change in aerobic capacity resulting from the therapy. During the recovery stage following exercise, the oxygen consumed, or equivalently the oxygen uptake, is above normal resting levels. The total oxygen consumed from onset of recovery until the pre-exercise level is reached is referred to as the recovery oxygen uptake. There are two components to recovery oxygen uptake: a fast component indicative of a quick drop in elevated oxygen consumption immediately after the cessation of activity, and a slower phase of recovery referred to as the slow component. For a given work level, the recovery oxygen uptake is less for more aerobically fit individuals and the total time of elevated oxygen uptake is an important measure of a patient's level of physical fitness. Recovery oxygen uptake duration may also be evaluated in determining the efficacy of therapy in CHF patients.

It is accordingly a principal purpose of the present invention to provide an implantable electronic device capable of measuring and storing the aerobic capacity of the patient in whom the device is implanted.

SUMMARY OF THE INVENTION

The implantable medical device of the present invention includes means for assessing a patient's aerobic capacity. The device comprises a fluid impervious, tissue compatible housing containing a battery power supply and electronic circuitry powered by the battery. The electronic circuitry preferably includes an accelerometer for sensing physical movements of a patient's body and for producing electrical signals relating thereto. The circuitry also includes means for sensing respiratory parameters of the patient. The information from the accelerometer and from the respiratory sensing means (which may also comprise the accelerometer) may then be used to compute the time required following a period of physical exercise and the cessation thereof for the respiratory parameter to return to a predetermined level associated with the patient's rest state. As mentioned, this time interval corresponds to the patient's aerobic capacity. Alternatively, rather than measuring the time for the heavy breathing to subside, it is also possible to compute the rate of change of the respiratory parameter following a period of physical exercise and the cessation thereof. For example, the rate of change or slew rate of minute ventilation with respect to time is also an indicator of the patient's fitness level.

The slew can be calculated immediately post-exercise and closer to the end of recovery allowing for calculation of the fast and slow components of the recovery phase. In addition, the integral of the respiratory parameters could also be determined and stored for reference.

The measured time value and/or time rate of change may be computed and stored at periodic intervals for later read-out, via a telemetry link, when the implanted device is interrogated by an external monitor/programmer module. Such history becomes valuable in assessing the efficacy of any therapy which may be rendered at various points in time.

The means for sensing respiratory parameters may include the accelerometer along with signal processing circuits for extracting from the accelerometer signal motion artifacts occasioned by breathing. Alternatively, a transthoracic impedance signal may be demodulated to derive tidal volume and respiratory rate information from which minute volume may be calculated.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which.

DESCRIPTION OF THE PREFERRED EMBODIMENT

Figure 1:
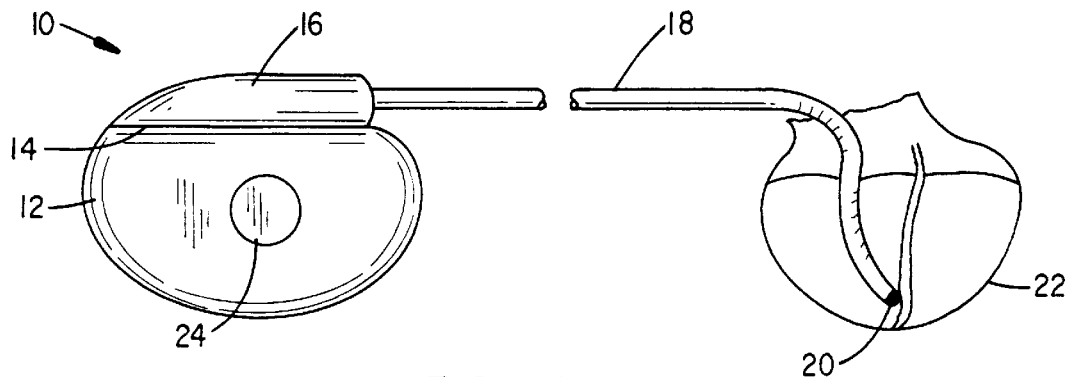
FIG. 1 illustrates an implantable cardiac rhythm management device incorporating the aerobic capacity monitoring feature of the present invention.

Referring to FIG. 1, there is indicated generally by numeral 10 an implantable medical device, such as a pacemaker or defibrillator, that includes a hermetically sealed housing 12 often times referred to as a "can" because it is made of a suitable metal such as titanium. Contained within the housing or can 12 is electronic circuitry as well as a battery power supply. Affixed to the header 14 of the can 12 is a lead barrel 16 containing contacts (not shown) that are connected via feedthrough pins to the circuitry within the can 12. Those skilled in the art of manufacturing implantable cardiac rhythm management devices, such as pacemakers and defibrillators, are thoroughly familiar with techniques for creating moisture impermeable, body-compatible devices for housing electronic circuitry. The implant device 10 is shown as being connected by a conventional pacing lead 18 to an electrode 20. The can 12 is preferably coated with a suitable insulator, such as a Silastic coating over its entirety except for one or more small predetermined areas 24 where the can is exposed to body tissue and can function as a return electrodes.

Figure 2:
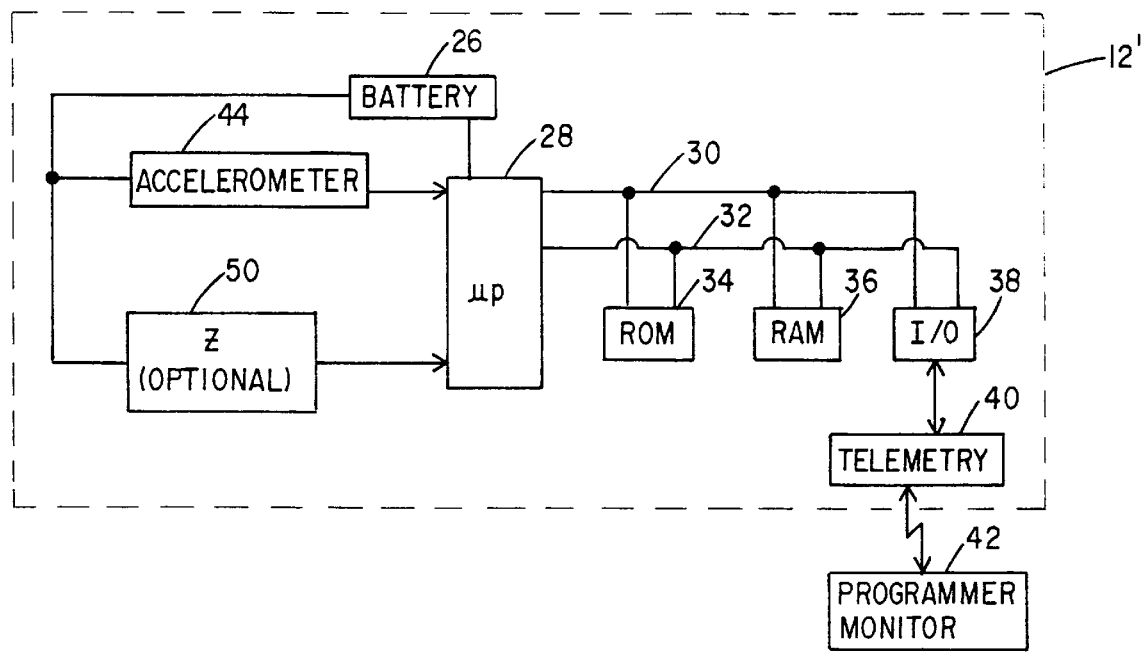
FIG. 2 is a block diagram of the portion of the cardiac rhythm management device of FIG. 1 utilized in deriving, storing and later telemetering information relating to aerobic capacity of a patient.

Referring next to FIG. 2, there is shown a block diagram of the circuitry contained within the housing 12 for implementing the aerobic capacity monitoring feature of the present invention. In FIG. 2, the housing 12 is represented by a broken line box 12'. Shown included within the housing is a battery 26, preferably a lithium iodide battery which exhibits long life with no out-gassing. The battery is connected to an integrated circuit microprocessor 28 to provide the requisite operating potential thereto. The microprocessor 28 includes an address bus 30 and a data bus 32 and connected across these two buses are a ROM 34, a RAM 36 and an input/output interface module 38. As is also conventional, the ROM will typically store a program of instructions executable by the microprocessor 38 for performing arithmetic and logical functions on operands applied to it. The RAM memory 36 stores various programmable parameters and intermediate computations carried out by the microprocessor. The input/output interface (I/O) 38 provides buffering of data read out from the RAM memory under control of the microprocessor 28 for delivery external to the body via a telemetry link 40. A programmer/monitor module 42, which may itself comprise a personal computer having a keyboard for data entry and a display can be used to further process and present information read out from the implanted device. It also permits medical personnel to alter programmable parameters stored in RAM 36, again via the telemetry link 40.

Also contained within the housing 12 is an accelerometer chip 44 that provides an electrical signal train to an input of the microprocessor proportional to body movements sensed by the accelerometer. While not shown in FIG. 2, the accelerometer module 44 may include suitable filtering and signal processing circuitry as well as an A/D converter. The A/D converter may also be a part of the microprocessor 28.

Figure 3:
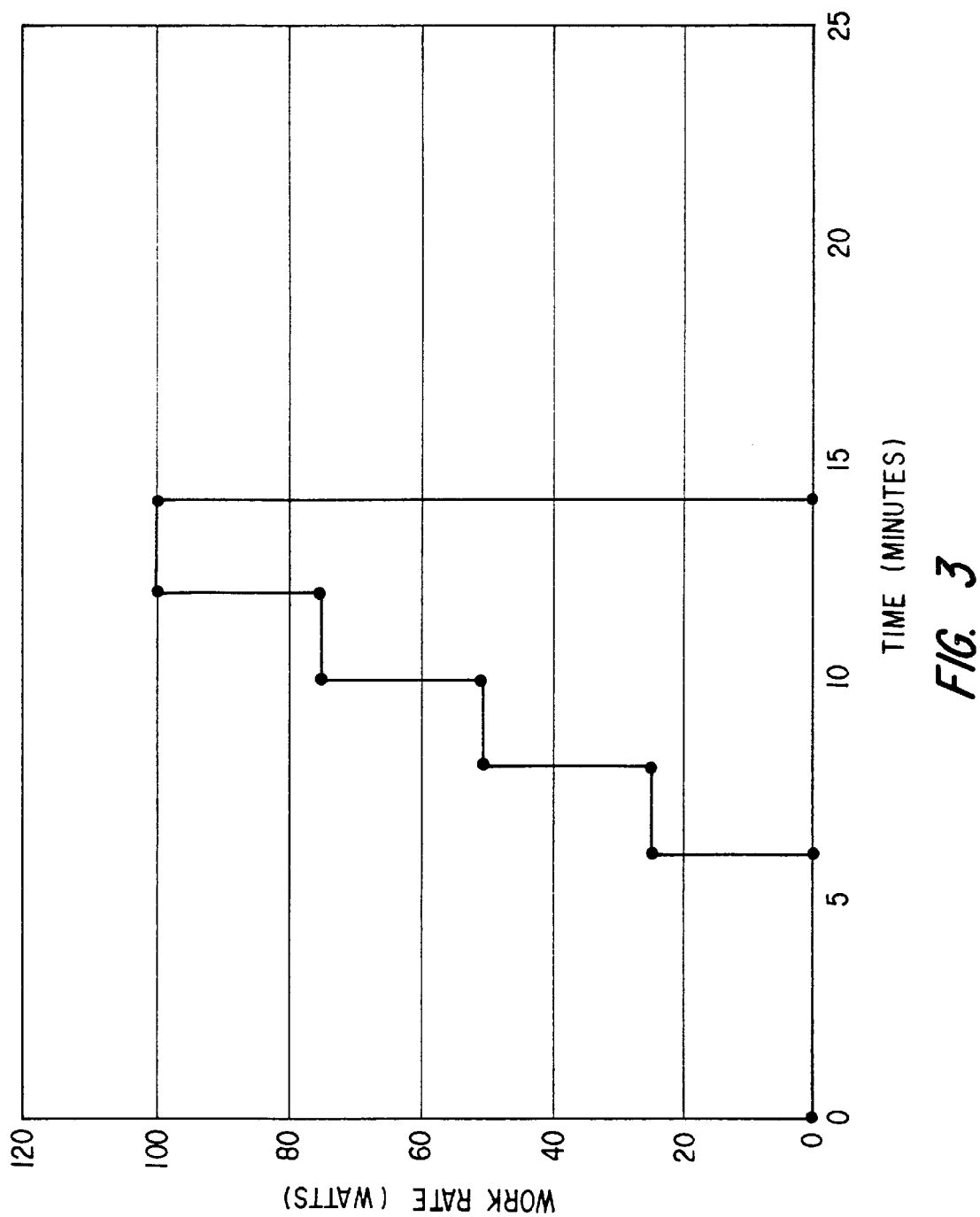
FIG. 3 is a plot of patient activity versus time.

FIG. 3 is a plot of work rate vs. time defining an exercise protocol for a patient. For the first six minutes, the patient is at rest, sitting in a chair or the like. At the six-minute point, the patient is placed on an ergometer and made to exercise at a 25 watt work rate for two minutes. At that point, the work rate is then increased to 50 watts for another two minutes before the work rate is elevated to 75 watts. The patient is made to exercise at the 75 watt rate for another two minutes and then the work rate is increased to 100 watts. At the conclusion of the two minute exercise at 100 watts, the patient again is put at rest.

Figure 4:
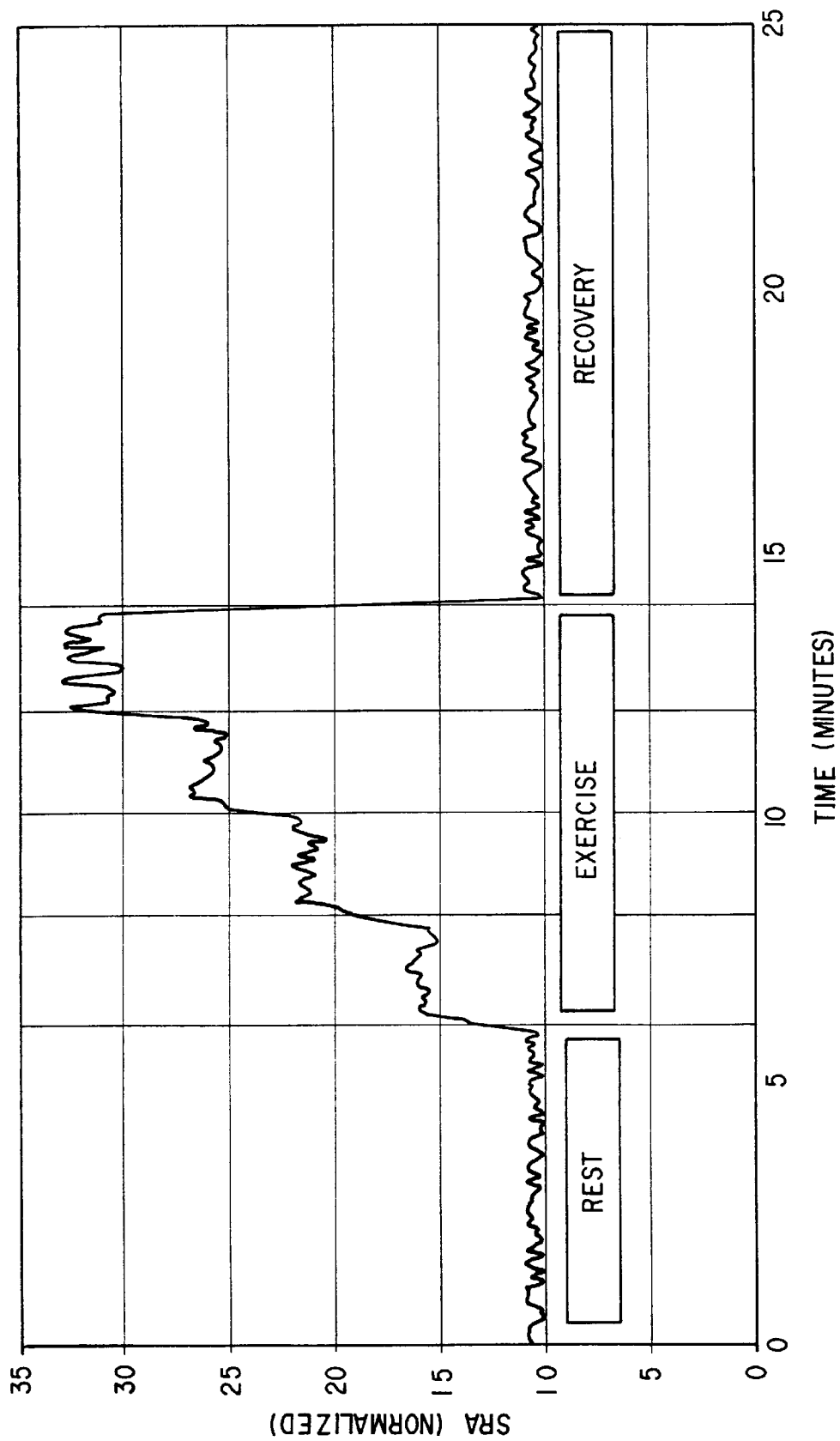
FIG. 4 illustrates a sensor rectified average derived from the accelerometer sensor during the exercise protocol illustrated in FIG. 3.

Referring to FIG. 4, the signal processed analog output from the accelerometer 44 corresponding to the above exercise protocol is illustrated. With the patient initially at rest, the amplitude of the accelerometer output excursions remains relatively low. At time, T=6 min., the patient is allowed to begin to exercise, such as by walking on a treadmill, working out on a stair climber or, in the case of severely infirmed CHF patients, by merely walking down a hallway or the like. The length of the exercise period will generally be sufficient to elevate the patient's respiration rate and depth.

Figure 5:
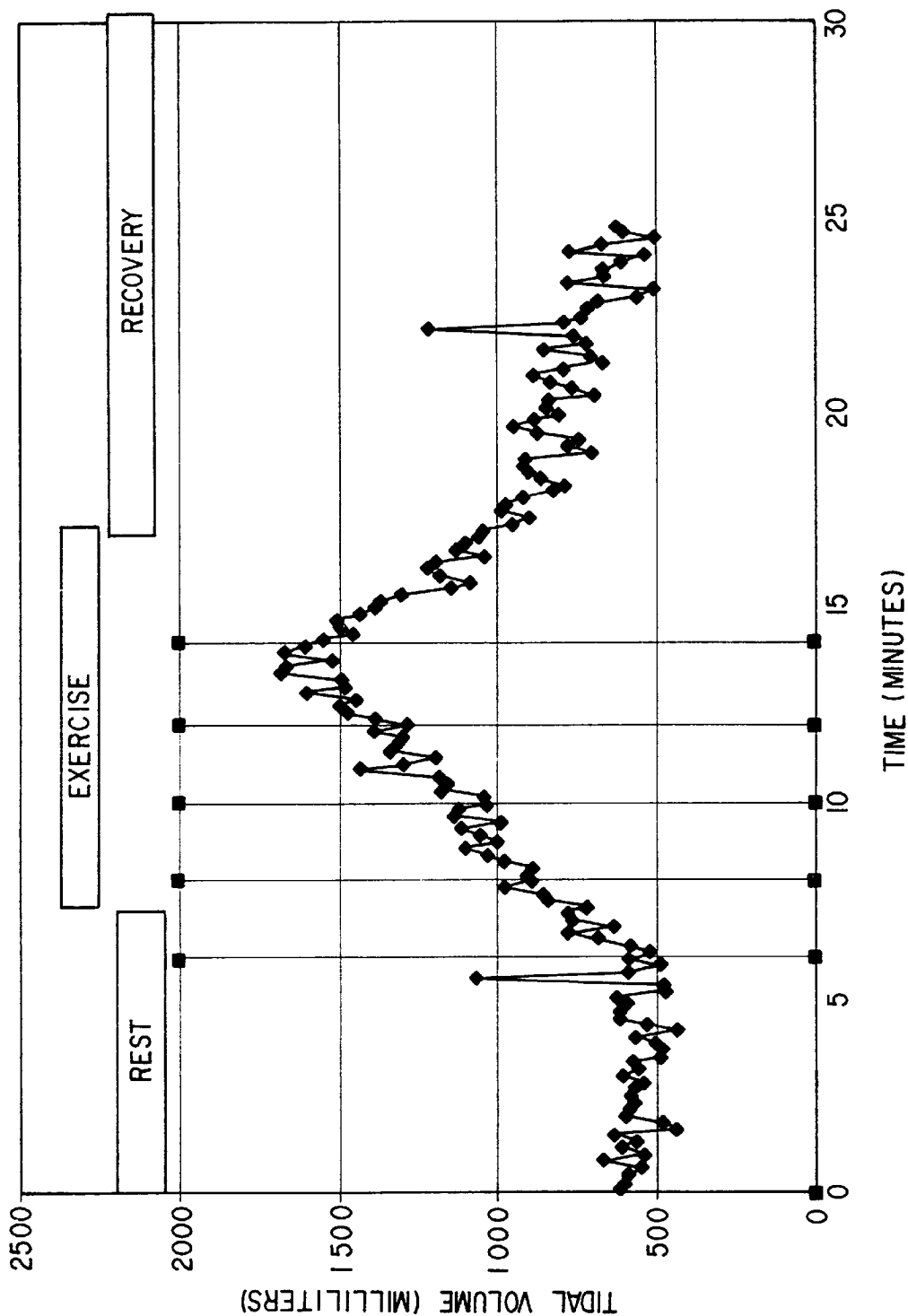
FIG. 5 a plot of tidal volume versus time corresponding to the activity plot of FIG. 3.

FIG. 5 is a plot of the patient's tidal volume over time and which is correlated timewise with the activity plot of FIG. 3. At the end of the exercise period, at T=14 min., the amplitude of the accelerometer output (FIG. 4) drops noticeably to a resting level as does tidal volume.

Figure 6:
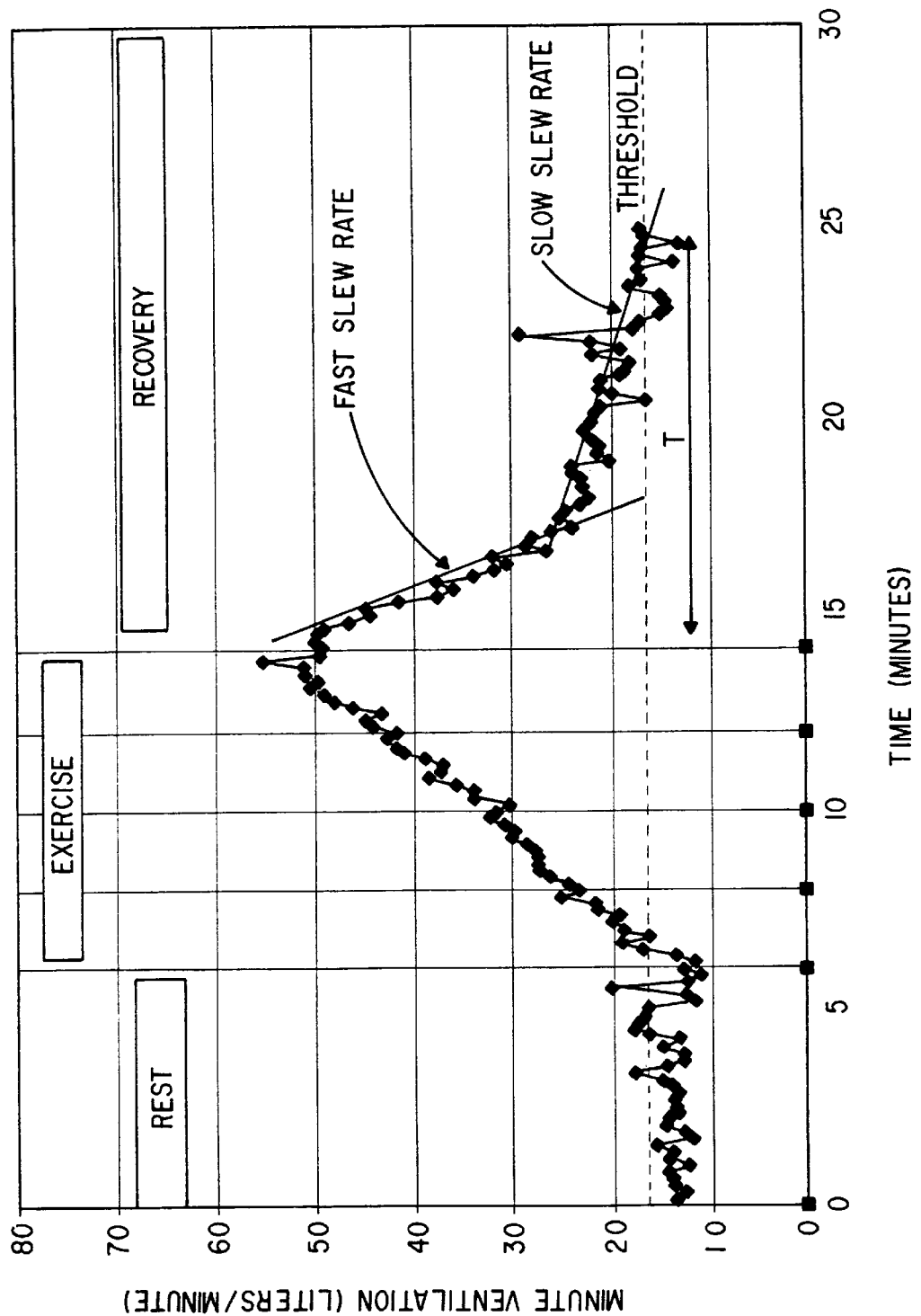
FIG. 6 is a plot of the patient's minute ventilation versus time corresponding to the exercise protocol depicted in FIG. 3.

Referring to FIG. 6, during exercise, the patient's minute ventilation increases to a maximum and, at the conclusion of the exercise, at T=14 min., it begins to fall off. The time that it takes for the minute ventilation to return to a predetermined level, such as its steady state rest level or some percentage thereof, is an indicator of oxygen debt accrued over the period of exercise.

Thus, FIGS. 4 and 5 represent two separate and independent measurements of physical activity. In the plot of FIG. 6, the time, T, for the minute ventilation curve 48 to drop to a predetermined percentage of the steady state rest value comprises the payback time and the length of the interval is an indicator of the relative physical fitness of the patient. For a given workload, the longer the interval, the less physically fit is the patient. In addition or alternatively, the total recovery minute ventilation can be calculated. This is equivalent to the integral of the minute ventilation parameter over time. Again, for a given workload, the larger the integral, the less physically fit the patient.

Instead of measuring the time interval, T, as shown in FIG. 6, another indicator of fitness is the slope or rate of change of the curve 48. The steeper the slope, the more healthy the patient. Still another measure of the fitness of the patient would be the area under the curve segment 48 with a large area being indicative of a lack of fitness. As mentioned earlier, the slew rate can be computed immediately post-exercise and then later close to the end of the recovery period so that calculations can be made of the fast and slow components comprising the recovery phase. In addition, the integral of the respiratory parameters during predetermined intervals can be calculated and stored for later readout and analysis in assessing the patients overall fitness.

As those skilled in the art appreciate, respiratory parameters can be derived directly from the acceleration signal using appropriate band-pass filtering. By choosing a pass band in a range from 0.05 to 1.0 Hz, body movement due to respiration is isolated. In particular, the variations in the accelerometer output in this frequency band provides both respiratory rate and tidal volume information from which minute volume can be computed. Alternatively or as an option, an impedance sensor 50 may be included in the circuitry contained within the housing 12. The impedance sensor may be like that described in the Salo et al. U.S. Pat. No. 4,686,987 wherein a high frequency carrier signal from an oscillator is applied between two spaced electrodes, here the electrode 24 which is typically located in the pectoral region of the body, and the electrode 20 located at the apex of the right ventricle. This carrier signal becomes modulated by inspiratory and expiratory movements of the diaphragm. By appropriate filtering and other signal processing techniques, it is possible to obtain signals having a strong linear relation to tidal volume, respiratory rate and to compute minute ventilation from these parameters. As those skilled in the art appreciate, it is not necessary to calibrate the sensor relationship to tidal volume as the resting or non-exercise level can be determined by long term observation and the exercise state discerned by a relative increase over the resting level.

The microprocessor 28 is programmed to sense the cessation of an exercise session and when this event is detected, a timer is initiated which continues to run until the respiratory signal (minute ventilation) drops either to a rest level that prevailed at the start of the test or to a predetermined percent thereof which may be programmed by the physician. As mentioned earlier, the length of the time interval is an indicator of oxygen debt.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. An implantable medical device for assessing a patient's aerobic capacity comprising, in combination:
    (a) accelerometer means for sensing physical movements of the body of a patient in whom the device is implanted;
    (b) means for sensing respiratory parameters of the patient; and
    (c) means for measuring one of
        (i) the time required following a period of physical exercise and cessation thereof for the respiratory parameter to return to a predetermined level associated with a patient's rest state, and
        (ii) the rate of change of the respiratory parameter following a period of physical exercise and cessation thereof.

2. The implantable medical device as in claim 1 wherein the means for sensing respiratory parameters comprises: signal processing means coupled to the accelerometer means for isolating body movements due to respiratory activity.

3. The implantable medical device as in claim 1 wherein the means for sensing respiratory parameters comprises: means for sensing thoracic impedance; and signal processing means coupled to the impedance sensing means for recovering a signal component proportional to minute ventilation therefrom.

4. The implantable medical device as in claim 1 and further including means for telemetering the measured one of time and rate of change to an external monitor.

5. The implantable medical device as in any one of claims 1–3 wherein the respiratory parameter is selected from a group consisting of minute ventilation, tidal volume and respiratory rate.

6. The implantable medical device as in claim 5 wherein the respiratory parameter, following a period of exercise and cessation thereof, exhibits a relatively fast changing component followed by a relatively slow changing component and the means for measuring measures the rate of change of said fast changing and slow changing components.

7. An implantable medical device for assessing a patient's aerobic capacity comprising, in combination:
    (a) a body fluid impervious, tissue compatible housing containing a battery and electronic circuitry powered by said battery, said circuitry including
        (i) an accelerometer for sensing physical movements of a patient's body and producing electrical signals relating thereto,
        (ii) means for deriving from the electrical signals a component corresponding to the patient's respiratory activity, and
        (iii) means for measuring a time interval following cessation of a period of physical exercise for the component corresponding to respiratory activity to return to a predetermined value.

8. The implantable medical device as in claim 7 and further including means for storing a maximum value of the component corresponding to the patient's respiratory activity.

9. The implantable medical device as in claim 7 wherein the circuitry further includes means for storing the time interval.

10. The implantable medical device as in claim 9 wherein the circuitry further includes telemetry means for transmitting the stored time interval to an external monitor.

11. An implantable medical device for assessing a patient's aerobic capacity comprising, in combination:
    (a) a body fluid impervious, tissue compatible housing containing a battery and electronic circuitry powered by said battery, said circuitry including
        (i) an accelerometer for sensing physical movements of a patient's body and producing electrical signals relating thereto,
        (ii) means for sensing thoracic impedance and deriving therefrom a signal component corresponding to the patient's respiratory activity; and
        (iii) means for measuring a time interval following cessation of a period of physical exercise for the component corresponding to respiratory activity to return to a predetermined value.

12. The implantable medical device as in claim 11 wherein the circuitry further includes means for storing the time interval.

13. The implantable medical device as in claim 11 wherein the circuitry further includes telemetry means for transmitting the stored time interval to an external monitor.

* * * * *